United States Patent [19]

Mansour

[11] Patent Number: 4,665,024

[45] Date of Patent: May 12, 1987

[54] FLUORESCENT GRAM STAIN

[75] Inventor: James D. Mansour, Raleigh, N.C.

[73] Assignee: Becton, Dickinson and Company, Franklin Lakes, N.J.

[21] Appl. No.: 656,627

[22] Filed: Oct. 1, 1984

[51] Int. Cl.$^4$ .......................... C12Q 1/04; C12Q 1/02; C12Q 1/14; G01N 21/64
[52] U.S. Cl. ......................................... 435/34; 435/29; 435/36; 435/802; 435/808; 435/837; 435/849; 435/852; 435/857; 435/882; 435/883; 435/885; 436/800; 250/461.2
[58] Field of Search ..................... 435/29, 34, 36, 802, 435/808, 882, 883, 885, 837, 849, 852, 857; 436/800; 250/461.2

[56] References Cited

U.S. PATENT DOCUMENTS

| | | | |
|---|---|---|---|
| 4,094,745 | 6/1978 | Scholefield | 436/800 |
| 4,126,516 | 11/1978 | Messing et al. | 195/103.5 R |
| 4,225,669 | 9/1980 | Melnick et al. | 435/29 |
| 4,492,752 | 1/1985 | Hoffman et al. | 435/7 |
| 4,508,821 | 4/1985 | Mansour et al. | 435/39 |

OTHER PUBLICATIONS

Matsuyama, T., Staining of Living Bacteria with Rhodamine 123, FEMS Micro. Letters, 21 (1984) 153–157.
Govorunov, et al., Microbiology (1982) 51, pp. 587–589, Study of Permeability of *E. coli* Membrane to Ethidium Bromide.

*Primary Examiner*—Robert J. Warden
*Assistant Examiner*—L. Krawczewicz
*Attorney, Agent, or Firm*—Richard E. Brown

[57] ABSTRACT

A method to determine the Gram sign of microorganisms includes staining the microorganisms with a plurality of fluorescent dyes, applying excitation energy to the stained microorganisms, and observing the color of the fluorescence emission of the stained microorganisms. Gram-positive and Gram-negative microorganisms stain different colors, and assignment of the Gram sign may be made on the basis of the color of the stained microorganisms.

19 Claims, 1 Drawing Figure

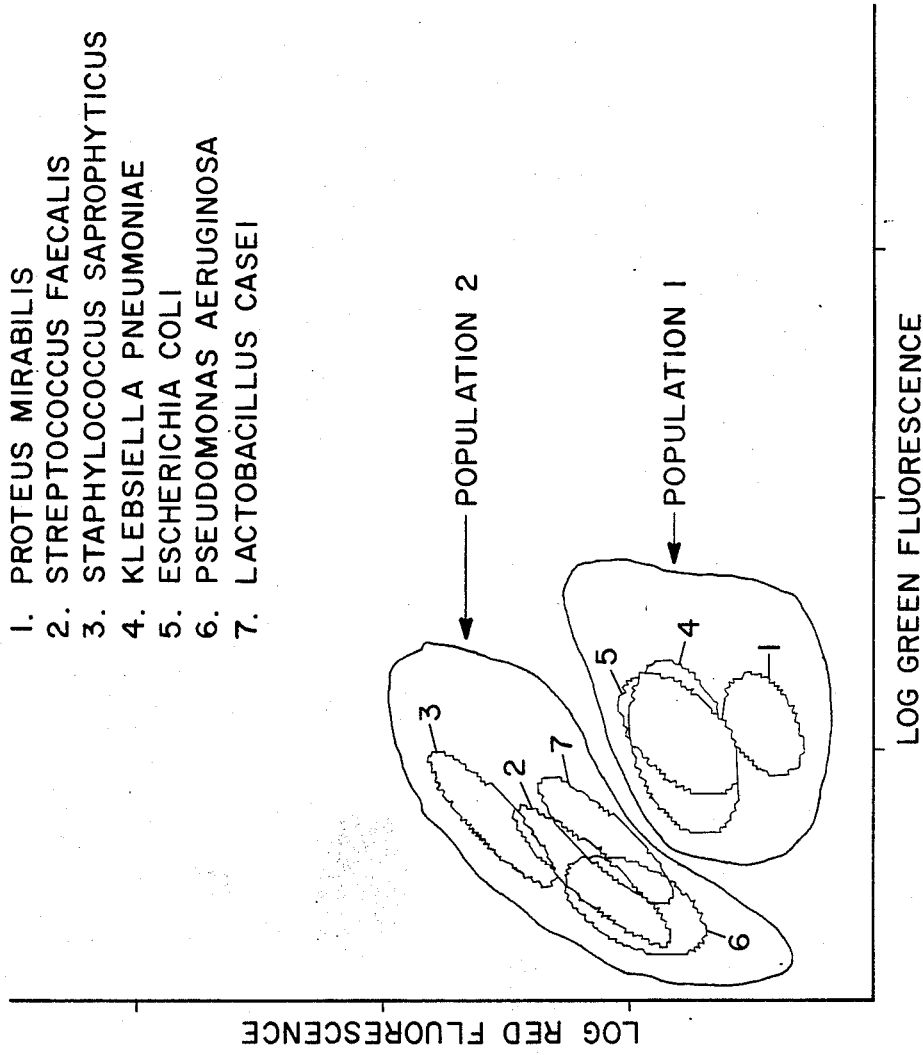

FLUORESCENT GRAM STAIN

BACKGROUND OF THE INVENTION

1. Field of the Invention

This invention relates to the staining of microorganisms. More particularly, it relates to the determination of the Gram sign by staining the microorganisms with a fluorescent dye or dye combination.

2. Description of the Prior Art

The Gram stain is one of the most widely used and important stains in microbiology. It permits the differentiation of microorganisms into two groups, conventionally referred to as Gram-positive and Gram-negative, based on the color of the stained organism at the conclusion of the staining protocol. In the Gram stain procedure, microorganisms on a cover slide are contacted with aqueous crystal violet, treated with iodine-potassium iodide solution, decolorized with alcohol or an ether-acetone mixture, counterstained with safranin O, dried, and examined. Gram-positive microorganisms retain the crystal violet and are thereby stained blue-violet. The Gram-negative microorganisms are completely decolorized by the organic solvent and show only the red color of the subsequently applied counterstain.

The determination of the Gram sign of a microorganism by the original procedure or any of the many subsequently described modifications is not a routine operation. In order to ensure accurate results, training, skill, proper technique and attention to detail are required. As a consequence, alternative procedures for Gram sign determination have been sought.

U.S. Pat. No. 4,225,669 to Melnick discloses a composition for staining both Gram-negative and Gram-positive microorganisms comprising a chelating agent and a non-fluorescent dye operative at a basic or neutral pH. Determination of the Gram sign may be carried out subsequent to staining by an acid wash which decolorizes the Gram-positive microoganrisms.

Attempts to adapt staining with fluorescent dyes to Gram sign determinations have been disclosed. Staining of microorganisms with fluorescent dyes is well known and Gram-negative and Gram-positive microorganisms show different taining characteristics with fluorescent dyes. Govoronov et al., Microbiology 51, 587 (1982) reported that ethidium bromide (EB) does not stain intact *E. coli* cells because the dye does not penetrate the cell membranes, but that staining does occur if carried out in the presence of ethylenediamine tetraacetic acid, EDTA. Matsuyama, Microbiology Letters 21, 153 (1984), observed that rhodamine 123 stained twelve Gram-positive bacteria, but seven of fourteen Gram-negative stains were sparsely stained. One of the Gram-negative strains, *Salmonella minnesota*, stained only after treatment with EDTA.

U.S. Pat. No. 4,094,745 to Scholefield teaches a method for staining microorganisms in food samples with a fluorochrome in the presence of phosphate ions. A protocol to detect non-viable Gram-positive and Gram-negative microorganisms in a milk sample and to determine the Gram sign includes heating the microorganims in the presence of hydrochloric acid.

U.S. Pat. No. 4,126,516 to Messing et al. discloses a growth-based method for determination of the Gram sign of an unknown microorganism. The organism is cultured in/on a growth medium containing a lipophilic fluorescent material. During growth, Gram-negative microorganisms, having a higher cell membrane lipid content, incorporate more of the lipophilic dye than Gram-positive microorganisms which have a lower cell membrane lipid content. The Gram sign of the unknown is assigned by analysis of its fluorescence emission as compared with the fluorescence emission from known Gram negative and Gram-positive controls cultured under identical conditions.

SUMMARY OF THE INVENTION

The present invention comprises a method for the determination of the Gram sign of microorganisms by stain in the microorganisms with one or more fluorescent dyes, applying excitation energy to the stained microorganisms, observing the color of the fluorescence emission of the stained microorganisms, and assigning the Gram sign on the basis of the color. The color of the fluorescence emission may be observed by fluorescence microscopy, flow cytometry or other like techniques.

In one embodiment of the invention, the microorganisms are contacted with a single fluorescent dye, whereby the Gram-positive microorganisms are stained and the Gram-negative microorganisms remain virtually unstained.

In a preferred embodiment of the invention, the microorganisms are stained with two or more fluorescent dyes. The dyes may be added sequentially or simultaneously, and the sample may be incubated briefly after the dyes are added, or between dye additions. If desired, the staining may be carried out in the presence of a staining buffer.

In a particularly preferred embodiment of the invention, the microorganisms are stained in a fluid sample. The fluid sample may be, for example, a body fluid sample containing microorganisms, such as urine, or it may be a liquid growth medium into which the microorganisms are inoculated and, if desired, allowed to grow before staining, or it may be a vehicle, such as water or saline, in which the microorganisms are suspended after transfer from another source, as, for example, from a solid growth medium.

The method of the present invention provides significant advantages over conventional methods for determination of the Gram sign. In the original Gram stain and all modifications thereof, overstaining or over-decolorizing are problems which may give the wrong result. Great care must be exercised to stay within the recommended limits for all reagent quantities and time durations for the various steps, and as a consequence, Gram-positive and Gram-negative controls are recommended. The method of the present invention avoids such restrictions, is a substantially faster and less complicated protocol, and does not require a decolorizer or mordant. No time consuming growth step is necessary. No harsh reagents or conditions, such as acid, alkali or heat which may affect the viability of the microorganisms are required. The staining may be done in a wet preparation rather than the conventional dry smear, and is therefore far less messy. Objective results may be obtained by flow cytometry which are more accurate than subjective results obtained conventionally with a microscope.

BRIEF DESCRIPTION OF THE FIGURE

The FIGURE is a graph of flow microfluorometry (a more specific form of flow cytometry) data which shows the determination of the Gram sign of microorganisms by the method of the invention.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention, and is not to be limited to the embodiments illustrated. The scope of the invention will be measured by the appended claims and their equivalents.

The present invention is a method for determination of the Gram sign of microorganisms by staining with a plurality of fluorescent dyes wherein Gram-positive microorganisms stain one color and Gram-negative microorganisms stain a different color. The Gram sign of any microorganism can be determined by the method of the invention, as, for example, Gram-positive microorganisms such as *Staph. aureus, Bacillus megaterium, Staph. saprophyticus, Strep. faecalis, Staph. epidermidis, L. casei* and the like, and Gram-negative microorganisms such as *E. coli, Proteus mirabilis, Pseudo. aeruginosa, Klebs. pneumoniae* and the like.

The microorganisms to be fluorescently stained for Gram sign determination may be from any source. For example, they may be present in a body fluid. Thus, it may be desired to determine the Gram sign of microorganisms in a urine sample from a patient having, or suspected to have, bacteriuria, or in a blood sample from a bacteremic patient. In the latter case, the microorganisms may be stained after suitable treatment of the blood, such as, for example, by removal of the formed elements. For purposes of illustration of the present invention, it is convenient to grow microorganisms in a suitable medium to mid-log phase and use these microorganisms for fluorescent staining. It is understood, however, that microorganism growth is not a feature of the invention.

The microorganisms may be stained directly on a microscope slide, or, preferably on a suspension of the microorganisms in a suitable fluid. The fluid may be a liquid growth medium, such as colombia broth, thioglycolate broth, Mueller-Hinton broth, or, preferably, trypticase soy broth, as for example, Trypticase Soy Broth ™, BBL Microbiology Systems, Cockeysville, Md. (hereinafter referred to as TSB ™) into which the microorganisms have been inoculated, and, if desired, grown. Alternatively, the microorganisms may be isolated from the liquid growth medium or from a body fluid such as urine or blood by any suitable technique, such as filtration or centrifugation, and resuspended in a different fluid, such as a buffer, water, or saline. In another embodiment of the invention, the microorganisms may be transferred from a solid growth medium, such as for example, trypticase soy agar, colombia agar or MacConkey agar, and suspended in the fluid for staining.

The microorganisms may be present in the fluid suspension at a concentration per milliliter of from about $1 \times 10^4$ to $1 \times 10^{10}$ colony forming units (cfu), preferably from about $1 \times 10^5$ to $1 \times 10^8$ cfu/ml. The microorganisms in suspension in the fluid are stained with a combination of fluorescent dyes. Any suitable dye combination may be used. Preferable dye combinations are EB-acridine orange (AO) and EB-thioflavin T (TT). The dyes are preferably added to the fluid suspension as stock solutions of from about 0.0001 to about 0.01%, preferably about 0.001% in a suitable solvent, preferably water. (All percentages used herein are by weight unless otherwise indicated.) The amount of stock solution of the dyes to be added will be calculated to provide a final dye concentration of from about 1 to about 1000 ug/ml, preferably from about 2.5 to 100 ug/ml.

The dyes may be added simultaneously or sequentially. In either case, an optional incubation step, as described below, may be carried out after addition of the dyes. In addition, if the dyes are added sequentially, the mixture of microorganisms in fluid suspension may be incubated between dye additions. Incubation may be carried out for about 1 to 60, preferably for about 10 to 20 minutes. The temperature of incubation may be from ambient to about 50° C. Preferably, incubation is carried out at ambient temperature. It is understood that the aforementioned incubation periods serve to enhance dye absorption and are not concerned with promoting organism growth.

In some cases, it is desirable to add a staining buffer to the fluid suspension of microorganisms before dye addition. Any suitable buffer may be used. Exemplary of buffers which may be used is an aqueous composition containing sodium borate, EDTA, formaldehyde and a surface active agent. Any suitable surface active agent, such as Triton X-100 (trademark of Rohm and Haas Co. for octyl phenoxy polyethoxyethanol), may be used. These reagents may be present in the buffer in concentrations of 40–200 mM, 24–100 mM, 0.02 to 0.1% and 0.02 to 0.1% by volume.

The staining buffer and dyes may be combined in a staining composition and the composition added to the suspension of microorganisms. The staining composition may be prepared by adding the fluorescent dyes to the staining buffer. The dyes are conveniently added to the buffer as the aforementioned stock solutions and are added in sufficient quantity to provide final dye concentrations in the staining composition of from about 1 to 100 ug/ml. The pH of the staining composition may be adjusted with an alkali metal hydroxide to 7–10, preferably 8.5 to 9.2. Sufficient staining composition is added to the suspension of microorganisms to provide a final concentration of dye in the fluid suspension of microorganisms of from about 1 to 1000, preferably 2.5 to 100 ug/ml, as described above.

The stained sample may be analyzed by detection of fluorescence emission. A suitable aliquot of the sample may be withdrawn and spread over a microscope slide and observed visually by fluorescence microscopy for about 1 minute to 1 hour. The wavelength of the incident light used for excitation depends on the dyes used, and may be from about 300 to 650, preferably from about 457 to about 488 nm.

Fluorescence emission may be detected at a wavelength above 520 nm, preferably from about 520 to 650 nm. When the dye combination used is EB-AO or EB-TT, microorganisms emitting substantially green fluorescence (520 to 550 nm) may be assigned as Gram-negative, and microorganisms emitting substantially orange fluorescence (580 to 650 nm) may be assigned as Gram-positive. Analysis may also be carried out by spectrofluorometry or, preferably, by flow microfluorometry techniques. These procedures are particularly advantageous when the microorganisms are present at low levels. In flow microfluorometry techniques, cells which are either naturally fluorescent or labeled with a fluorochrome, are passed, one at a time, through the focused beam from a light source, such as a laser or an arc lamp, whereby they are caused to emit fluorescent signals which are detected. A flow microfluorometry instrument such as a FACS Analyzer or a FACS IV Cell Sorter (FACS Division of Becton, Dickinson and Company, Sunnyvale, California) may be used. The sample is preferably passed through the beam at a rate of from about 0.05 ml/min to about 0.3 ml/min., preferably about 0.1 ml/min.

In accordance with the method of the invention wherein fluorescence emission is observed using a flow microfluorometer, data may be obtained using multiple parameters of analysis, as, for example, forward and 90° light scatter and red and green fluorescence emission. The data may be presented and studied using a linear scale or, preferably, a logarithmic scale, or, if desired, some parameters may be studied using a linear scale while others are studied using a log scale. The determination of suitable parameters of analysis and instrument settings are well known to those skilled in the art and no further details in these respects are needed for a complete understanding of the invention. The data collected may be displayed, for example, by plotting log red fluorescence emission vs. log green fluorescence emission. The Figure shows Gram-negative microorganisms located in one area of the graph and Gram-positive microorganisms located in a different area of the graph. The Gram sign of microorganisms may be assigned by the relative location of the microorganisms on the graph.

In an alternate embodiment of the invention, the microorganisms are stained with a single fluorescent dye which stains Gram-positive microorganisms in the absence of staining buffer, but does not stain Gram-negative microorganisms under the same conditions. Exemplary of dyes which may be used in this embodiment of the invention are 3,3'-dipentyloxacarbocyanine iodide, rhodamine 123, rhodamine B and, preferably, ethidium bromide. In this embodiment of the invention, light microscope may be used to identify the unstained Gram-negative microorganisms and fluorescence microscope may be used to identify the stained Gram-positive microorganisms.

The following examples are provided to further illustrate the invention, but are not to be construed in any way as limitative of the invention.

EXAMPLE 1

*E. coli, Staph. saprophyticus* and *Proteus mirabilis* were grown separately in TSB ™ to mid log phase. Aliquots of 350 ul of each culture were prepared in duplicate and added to separate tubes. One aliquot of each was treated with 100 ul of staining buffer*, the other aliquot of each was treated with 100 ul of normal saline, and all aliquots, after standing at room temperature for 2 minutes, were treated with 50 ul of a 100 ug/ml aqueous solution of EB. Twenty ul samples from each tube were spread over a microscope slide and observed under a fluorescent microscope. The microorganisms from the tubes containing staining buffer showed substantially green fluorescence emission. In the absence of staining buffer, gram-positive microorganisms (*Staph. saprophyticus*) were seen to be stained, but the gram-negative microorganisms (*E. coli* and *Proteus mirabilis*) remained unstained after 30 minutes at room temperature.
*sodium borate, sodium EDTA, formaldehyde and Triton X-100 at concentrations of 100 mM, 60 mM, 0.05% and 0.05% by volume respectively.

EXAMPLE 2

The six microorganisms listed in the chart below were grown to mid-log phase in TSB ™ and studies in the absence of staining buffer by the procedure of Example 1. The results of this experiment are summarized below in the chart and show the correlation between the known Gram sign and the observed fluorescence emission:

| Microorganism | Known Gram Sign | Staining Result* |
|---|---|---|
| E. coli | − | − |
| Staph. aureus | + | + |
| Klebs. pneumoniae | − | − |
| Pseudo. aeruginosa | − | − |
| Bacillus megaterium | + | + |
| Strep. faecalis | + | + |

*plus sign indicates the microorganisms were stained substantially orange; minus sign indicates the microorganisms were not stained.

EXAMPLE 3

The nine microorganisms listed in the chart below were streaked onto separate trypticase soy agar plates and the plates were incubated for 24 hours at 37° C. Nine tubes, each containing 450 ul of TSB ™, were inoculated with two colonies from each plate to give turbid suspensions of each microorganisms. The tubes were treated with 50 ul of a 100 ug/ml aqueous solution of EB. After 2 minutes at room temperature, 20 ul samples were removed from each tube and spread over microscope slides. The slides were observed under a fluorescent microscope. The results are summarized in the chart below:

| Microorganisms | Known Gram Sign | Staining Result* |
|---|---|---|
| E. coli | − | − |
| Staph. aureus | + | + |
| Bacillus megaterium | + | + |
| Staph. saprophyticus | + | + |
| Strep. faecalis | + | + |
| Staph. epidermidis | + | + |
| Proteus mirabilis | − | − |
| Pseudo. aeruginosa | − | − |
| Klebs. pneumoniae | − | − |

*plus sign indicates the microorganisms were stained sustantially orange; minus sign indicates the microorganisms were unstained.

EXAMPLE 4

*E. coli* and *Staph. aureus* were grown separately to mid log phase in TSB ™ and 400 ul of each cell suspension were added to separate tubes. Each tube was treated with 50 ul of a 100 ug/ml aqueous solution of EB. After 2 minutes at room temperature, each tube was treated with 50 ul of a 250 ug/ml aqueous solution of AO. After another 2 minutes at room temperature, 20 ul samples from each tube were spread over a microscope slide and observed under the fluorescent microscope. The gram-negative *E. coli* were stained substantially green and the gram-positive *Staph. aureus* were stained substantially orange.

EXAMPLE 5

*Proteus mirabilis* and *Strep. faecalis* were grown separately to mid log phase in TSB ™ and 350 ul of each cell suspension were added to separate tubes and treated with 50 ul of staining buffer and 50 ul of a 200 ug/ml aqueous solution of TT. After 2 minutes at room temperature, 50 ul of a 100 ug/ml aqueous solution of EB were added to each tube. After 2 minutes at room temperature, 20 ul samples from each tube were spread over a microscope slide and observed under the fluorescent microscope. The gram-positive *Strep. faecalis* were substantially orange and the gram-negative *Proteus mirabilis* were substantially green.

EXAMPLE 6

The nine microorganisms listed below in the chart were streaked onto separate trypticase soy agar plates and the plates were incubated for 24 hours at 37° C. Nine tubes containing 400 ul each of TSB TM were inoculated with one colony from each plate to give turbid suspensions of each microorganism.

The nine microorganisms were also grown separately to mid log phase in TSB TM, and 400 ul of each culture were added to separate tubes.

The eighteen tubes were treated with 50 ul of a 200 ug/ml aqueous solution of TT. After 2 minutes at room temperature, 50 ul of a 100 ug/ml aqueous solution of EB was added to each tube. After an additional 2 minutes at room temperature, 20 ul samples from each tube were spread over a microscope slide and observed under the fluorescent microscope. The results are given in the chart below:

| Microorganisms | Known Gram Sign | Color of Stained Microorganisms From Plate | From Mid-Log TSB TM |
| --- | --- | --- | --- |
| E. coli | − | green | green |
| Staph. aureus | + | orange | orange |
| Bacillus megaterium | + | orange | orange |
| Staph. saprophyticus | + | orange | orange |
| Strep. faecalis | + | orange | orange |
| Staph. epidermidis | + | orange | orange |
| Proteus mirabilis | − | green | green |
| Pseudo. aeruginosa | − | orange | orange |
| Klebs. penumoniae | − | green | green |

It is seen that, with the exception of *Pseudo. aeruginosa*, gram-positive microorganisms stained substantially orange and gram-negative microorganisms stained substantially green in this protocol.

EXAMPLE 7

*E. coli, Klebs. pneumoniae, Pseudo. aeruginosa, Proteus mirabilis, Lactobacillus casei, Staph. saprophyticus* and *Strep. faecalis* were grown separately in TSB TM to mid log phase. Aliquots of 350 ul of each culture were added to 0.5 ml of sterile filtered urine in separate tubes. Each tube was treated with 2.0 ml of a staining buffer-dye composition consisting of 100mM HEPES, (N-2Hydroxyethylpiperazine-N'-2-ethanesulfonic acid), 60 mM NaEDTA, 0.00625% Triton X-100, and 0.00625% formalin pH 8.0 containing 50 ug of TT and 25 ug of EB. The tubes were allowed to stand at room temperature for 15 minutes and the microorganisms analyzed on the FACS IV Cell Sorter. The excitation wavelength was 457 nm, and data were gathered using log forward scatter, log 90° scatter, log red fluorescence emission, and log green fluorescence emission. The data were displayed by plotting log red fluorescence vs. log green fluorescence and is similar to that shown in the Figure. It is seen that the seven bacterial clusters separated into two populations wherein the microorganisms in population 1 are more green than red and the microorganisms in population 2 are more red than green. With the exception of *Pseudo. aeruginosa,* Gram positive microorganisms appear in population 2 and Gram negative microorganisms appear in population 1.

Thus, the invention provides a method to determine the Gram sign of microorganisms based on staining with one or more fluorescent dyes. In a preferred embodiment of the invention, two fluorescent dyes are used wherein Gram-positive and Gram-negative microorganisms are stained different colors, and the Gram assignment is based on these colors. The method is clean and uncomplicated, and provides the Gram assignment much faster than by conventional Gram sign protocols or by prior art methods based on fluorescent staining.

What is claimed is:

1. A method for the rapid determination of the Gram sign of microorganisms in a fluid sample comprising adding ethidium bromide and another fluorescent dye to the sample to provide a mixture including fluorescently stained microorganisms, applying excitation energy to said mixture, observing the color of the fluorescence emission of said stained microorganisms, and assigning the positive Gram sign to said stained microorganisms which fluoresce substantially orange and the negative Gram sign to said stained microorganisms which fluoresce substantially green.

2. The method in accordance with claim 1 wherein Gram-positive microorganisms included in said fluid sample are selected from the group of microorganisms consisting of *Staphylococcus aureus, Staphylococcus saprophyticus, Bacillus megaterium, Streptococcus faecalis, Staphylococcus epidermidis,* and *Lactobacillus casei.*

3. The method in accordance with claim 1 wherein Gram-negative microorganisms included in said fluid sample are selected from the group of microorganisms consisting of *Escherichia coli, Proteus mirabilis,* and *Klebsiella pneumoniae.*

4. The method in accordance with claim 1 wherein said mixture is incubated prior to said observing step.

5. The method in accordance with claim 1 wherein said fluid is selected from the group of fluids consisting of water, buffer, normal saline, a liquid growth medium and a body fluid.

6. The method in accordance with claim 5 wherein said liquid growth medium is selected from the group of media consisting of trypticase soy broth, colombia broth, thioglycolate broth, and Mueller-Hinton broth.

7. The method in accordance with claim 1 which includes the step of transferring said microorganisms from a solid growth medium to said fluid sample prior to adding said fluorescent dyes.

8. The method in accordance with claim 7 wherein said solid growth medium is selected from the group of media consisting of trypticase soy agar, colombia agar, and MacConkey agar.

9. The method in accordance with claim 1 wherein said excitation energy is from about 300 to about 650 nm and said fluorescence emission generated by said fluorescently stained microorganisms is observed above 520 nm.

10. The method in accordance with claim 1 wherein the fluorescence emission of said stained microorganisms is observed by flow microfluorometry.

11. The method in accordance with claim 1 wherein the fluorescence emission of said stained microorganisms is observed by fluorescence microscopy.

12. The method in accordance with claim 1 further comprising adding a staining buffer to the sample prior to adding said fluorescent dyes.

13. The method in accordance with claim 12 wherein said staining buffer comprises sodium borate, formaldehyde, ethylenediamine tetraacetic acid and surface active agent.

14. A method for the rapid determination of the Gram sign of microorganisms in a fluid sample comprising adding ethidium bromide to the sample to provide a first mixture, incubating said first mixture, adding acridine orange to said first mixture to provide a second mixture, incubating said second mixture so that it includes fluorescently stained microorganisms, applying excitation energy to said second mixture, observing the color of the fluorescence emission of the stained microorganisms, and assigning the positive Gram sign to said microorganisms which fluoresce substantially orange and the negative Gram sign to said microorganisms which fluoresce subtantially green.

15. A method for the rapid determination of the Gram sign of microorganisms in a fluid sample comprising adding ethidium bromide and thioflavin T to the sample to provide a mixture, incubating said mixture so that it includes fluorescently stained microorganisms, applying excitation energy to said mixture, observing the color of the fluorescence emission of the stained microorganisms, and assigning the positive Gram sign to said microorganisms which fluoresce substantially orange and the negative Gram sign to said microorganisms which fluoresce substantially green.

16. The method in accordance with claim 15 wherein ethidium bromide and thioflavin T are added simultaneously.

17. The method in accordance with claim 15 wherein ethidium bromide is added to said sample subsequent to the addition of thioflavin T.

18. The method in accordance with claim 15 further comprising adding a staining buffer to said sample prior to adding ethidium bromide and thioflavin T, and observing said colors by flow microfluorometry means including logarithmic scale measurement of red and green fluorescence emission.

19. A method for the rapid determination of the Gram sign of microorganisms comprising adding a fluorescent dye selected from the group of dyes consisting of ethidium bromide, 3,3'-dipentyloxacarbocyanine iodide, rhodamine 123, and rhodamine B to the microorganisms to provide a mixture wherein Gram-positive microorganisms become fluorescently stained and Gram-negative microorganisms remain substantially unstained, observing said mixture under light microscopy means and fluorescence microscopy means, and assigning the positive Gram sign to said microorganisms which are observed to be stained and the negative Gram sign to said microorganisms which are observed to be unstained.

* * * * *